United States Patent [19]
Van Bramer

[11] Patent Number: 5,866,727
[45] Date of Patent: Feb. 2, 1999

[54] TETRAFLUOROETHYLENE SHIPPING/STORAGE MIXTURES

[75] Inventor: David John Van Bramer, Belpre, Ohio

[73] Assignee: E. I. du Pont de Nemours and Company, Wilmington, Del.

[21] Appl. No.: 965,203

[22] Filed: Nov. 6, 1997

[51] Int. Cl.$^6$ .................................................. C07C 17/42
[52] U.S. Cl. .......................................................... 570/122
[58] Field of Search ............................................... 570/122

[56] References Cited

U.S. PATENT DOCUMENTS 2,753,329  7/1956  Kroll et al. .............................. 570/122
5,345,013  9/1994  Van Bramer ............................ 570/102

*Primary Examiner*—Alan Siegel

[57] ABSTRACT

Tetrafluoroethylene is safely shipped or stored in the form of a liquid mixture with 35 to 65 mol % hexafluoropropylene.

3 Claims, No Drawings

TETRAFLUOROETHYLENE SHIPPING/STORAGE MIXTURES

BACKGROUND OF THE INVENTION

This invention relates to the safe storage and shipping of tetrafluoroethylene (TFE).

U.S. Pat. No. 5,345,013 discloses the explosivity of TFE under a number of modest temperature and pressure conditions. This patent provides an improvement over the prior method of rendering the TFE safe during storage and shipping, by providing the TFE in the form of an azeotrope with $CO_2$ instead of an azeotrope with HCl. The co-vaporization of the $CO_2$ along with TFE, by virtue of the azeotrope relationship between these compounds, protects the TFE against ignition. While the $CO_2$ azeotrope companion to the TFE is better than HCl because of the greater environmental friendliness of $CO_2$, the $CO_2$ still has to be separated from the TFE so that the TFE can be used as a monomer for making a fluoropolymer or for other chemical reaction.

The need exists for the ability to safely store or ship TFE without the accompaniment of an additional material that requires separation from the TFE before its use and disposal of the additional material.

SUMMARY OF THE INVENTION

The present invention satisfies this need by the process of shipping or storing the tetrafluoroethylene in the form of a liquid mixture with at least 35 mol % of hexafluoropropylene (HFP). The TFE and HFP may not need to be separated from each other before use (after shipping or storage) when they can be used as co-reactants in a chemical process. Alternatively, if separation is desired for separate use of these compounds, there is no disposal problem, because both compounds are useful in chemical reactions. The greater the proportion of HFP present in the liquid mixture, the greater the margin of safety against explosion. Preferably, the liquid mixture will not contain more than 65 mol % of HFP.

The invention may also be described as a container for long-term containment of TFE and containing the TFE in the form of the liquid mixture just described. Typically, the long-term containment will occur under conditions of varying temperature, but the temperature range to which the contained liquid mixture will normally be exposed will be from –50° C. to +55° C. The maximum of 55° C. is an international shipping standard, i.e. the highest temperature that could be encountered anywhere in the world during shipping of a product. By long-term containment is meant storage or transportation of the liquid mixture for at least 6 hours.

The HFP does not form an azeotrope with TFE and yet is sufficiently volatile to prevent the TFE from ignition during long-term containment.

DETAILED DESCRIPTION

TFE boils at –75.6° C. and HFP boils at –29.4° C. at atmospheric pressure (760 mm Hg, 101.3 kPa, absolute). These compounds can be mixed together as liquids but preferably as gases, which are then co-condensed to form a homogeneous liquid mixture in which the two compounds are fully miscible with one another. Another procedure would be to mix TFE gas into HFP liquid until the composition desired is reached. The liquid mixture can be made in one container and then transferred to the container to be used for storage or shipping.

The most common ignition source to which the container of liquid mixture will be exposed is a localized hot spot generated by such sources as localized overheating due to autopolymerization, possible spark discharge due to the buildup of static electricity, or an external heat source. The ignition test (Ignition Test) disclosed in the '013 patent is used to simulate this exposure and thus to qualify safety from ignition during storage or shipping within the temperature range that might be encountered during storage or shipping, i.e. –50° C. to +55° C. The liquid mixture is relatively safe from ignition as will be explained below. The most ignitable part of the contained liquid mixture is the gaseous TFE in the vapor space above the liquid in the container. Such vapor space is present to allow for expansion of the liquid mixture within the container as well as the buildup in gaseous pressure in the vapor space as the contents of the container become heated (up to 55° C.) during storage or shipping. The container will normally be filled "cold" e.g. at temperatures of 0° C., or colder, in which case some heating up of the contents of the container is to be expected. Warmer filling temperatures can be used. In any event, vapor space is left in the container to prevent the liquid mixture from completely filling the container even if the contents of the container were heated above 55° C., which in the case of further internal pressure increase could lead to catastrophic failure of the container. The vapor pressure within the container will generally be from 25 psia (0.17 MPa absolute) to 576 psia (4.0 MPa absolute), within the temperature range of –50° C. to +55° C.

The proportion of HFP present in the liquid mixture is selected so that sufficient HFP is present in the vapor space above the liquid in the storage or shipping container to prevent the TFE in the vapor space from igniting if or when exposed to intense heat as in the ignition test. It has been found that at least 35 mol % HFP present in the liquid mixture is desirable. The mole percents of HFP disclosed herein are based on the mole percents of the HFP and TFE totaling 100 mol %. Since TFE is more volatile than HFP, the concentration of HFP in the vapor space will be less than that in the liquid mixture. The relatively greater concentration of the HFP in the liquid mixture, coupled with the heat sink effect of the liquid mixture on exposure to a localized hot spot, makes the liquid mixture less susceptible to ignition than the vapor space above it, thus making the vapor space be the greatest point of danger. Thus, the Ignition Test is conducted with the Nichrome® wire positioned within the vapor mixture of TFE/HFP. In summary, electrical current is passed through this resistance wire to cause the wire to fuse, indicating a temperature of 1350° C. Exposure of the vapor mixture to the fused wire is carried out for about one sec (includes the time the electrical current is turned on), before the wire melts, breaking the electrical circuit. The temperature of the vapor mixture will be the temperature within the range of –50° C. and +50° C. selected for the test and the pressure will be the pressure that is expected for the particular composition being tested and at the temperature of the test. Ignition is indicated by an increase in pressure and temperature within the container in which the test is conducted.

As the vapor pressure in the vapor space increases from increasing temperature, however, the proportion of HFP in the vapor space also increases, providing greater safety from ignition of the TFE in the vapor space. The proportion of HFP in the liquid mixture can be very high, e.g. up to 99 mol %, but results in the shipment or storage of a relatively small amount of TFE, whereby the proportion of HFP in the liquid mixture is preferably no greater than 65 mol %. Preferably, at least 40 mol % of the liquid mixture is HFP and more preferably, 45 to 55 mol % of the liquid mixture is HFP. The proportion of HFP in the liquid mixture within the limits of providing safety from ignition, can be selected so as to provide the proportion of TFE and HFP desired for chemical interaction after shipping or storage to form a fluorochemical such as perfluoropentene. Alternatively, less HFP can be present than desired for the chemical interaction, but sufficient for safe storage and shipping, and the extra HFP can be added at the location where the mixture is to be used in a chemical reaction. At the temperatures encountered during shipping or storage, no chemical interaction occurs between the TFE and HFP components of the mixture (liquid or vapor). If separate use of the TFE and HFP components is desired after shipping or storage of the liquid mixture, the TFE and HFP can be separated from one another by using conventional separation methods such as distillation.

No less than 35 mol % HFP should be present in the liquid mixture because the critical temperature of the TFE/HFP mixture at about 34 mol % HFP concentration is about 55° C., which is a forseeable maximum temperature to which the contents of the container might be exposed under normal conditions during shipping or storage. Thus stored liquid mixtures containing about 34 mol % HFP or less could enter the supercritical state at 55° C., in which case the liquid mixture would no longer be present. The minimum of 35 mol % HFP in the liquid mixture gives some margin of safety.

Containers used for storing or shipping the TFE/HFP compositions used in the present invention can be any of those used for storing or shipping liquified gases and which are of materials of construction which do not react with the composition.

At various temperatures and with the TFE/ HFP liquid mixture containing varying amounts of HFP, the TFE/HFP vapor gives the following Ignition Test results:

| Temperature (°C.) | Mol % HFP | Pressure (kg/cm² abs) | Ignition |
|---|---|---|---|
| 55 | 36 | 40.1 | no |
| 55 | 35 | 40.5 | yes |
| 55 | 34 | 40.9 | yes |
| 45 | 36 | 33.9 | no |

-continued

| Temperature (°C.) | Mol % HFP | Pressure (kg/cm² abs) | Ignition |
|---|---|---|---|
| 45 | 35 | 34.3 | yes |
| 45 | 34 | 34.7 | yes |
| 35 | 36 | 27.9 | no |
| 35 | 35 | 28.2 | no |
| 35 | 34 | 28.6 | no |
| 35 | 25 | 31.5 | yes |
| 5 | 36 | 14.1 | no |
| 5 | 34 | 14.4 | no |
| 5 | 27 | 15.5 | yes |

These results represent an exploration of the effect of having a minimum proportion of HFP in the liquid mixture which in turn affects the amount of HFP in the vapor mixture above the liquid mixture. As a benchmark, pure TFE vapor in equilibrium with pure TFE liquid ignites (Ignition Test) at temperatures greater than −20° C. The results in the above table in the borderline supercritical region of 34 mol % HFP in the liquid are mixed. As the temperature increases, so does the ignitability of the vapor mixture. At as low as 27 mol % HFP in the liquid, the vapor mixture ignites even at the low temperature of 5° C. When 35 mol % of the liquid mixture is HFP, the vapor mixture does not ignite until the temperature is at 55° C. The preference for at least 40 mol % HFP in the liquid mixture provides a much greater margin of safety.

What is claimed is:

1. Shipping or storage container for long-term containment of tetrafluoroethylene, said container containing said tetrafluoroethylene in the form of a liquid mixture comprising said tetrafluorethylene and 35 to 65 mol % of hexafluoropropylene (HFP) and a vapor space above said liquid mixture, said vapor space containing a mixture of tetrafluoroethylene and hexafluoropropylene vapor from said liquid mixture.

2. The container of claim 1 wherein from 45 to 55 mol % HFP is present in said liquid mixture.

3. Process comprising shipping or storing tetrafluoroethylene in the form of a liquid mixture comprising said tetrafluoroethylene and 35 to 65 mol % of hexafluoropropylene.

* * * * *